(12) United States Patent
Yamada et al.

(10) Patent No.: US 8,877,519 B2
(45) Date of Patent: Nov. 4, 2014

(54) CHEMICAL SENSOR ELEMENT, SENSING APPARATUS, AND SENSING METHOD

(75) Inventors: Tomohiro Yamada, Yokohama (JP); Yoichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 564 days.

(21) Appl. No.: 12/738,228

(22) PCT Filed: Oct. 29, 2008

(86) PCT No.: PCT/JP2008/070144
§ 371 (c)(1),
(2), (4) Date: Apr. 15, 2010

(87) PCT Pub. No.: WO2009/057804
PCT Pub. Date: May 7, 2009

(65) Prior Publication Data
US 2010/0233825 A1   Sep. 16, 2010

(30) Foreign Application Priority Data

Nov. 2, 2007   (JP) ................................. 2007-286102

(51) Int. Cl.
*G01N 33/553* (2006.01)
*G01N 21/55* (2014.01)
*G01N 21/27* (2006.01)

(52) U.S. Cl.
CPC .............. *G01N 21/554* (2013.01); *G01N 21/27* (2013.01); *Y10S 436/805* (2013.01)
USPC .......................................... 436/525; 436/805

(58) Field of Classification Search
None
See application file for complete search history.

(56) References Cited

U.S. PATENT DOCUMENTS

| 7,399,445 | B2 | 7/2008 | Kuroda et al. | |
| 7,447,391 | B2 * | 11/2008 | Peled et al. | 385/12 |
| 7,684,044 | B2 | 3/2010 | Sekiguchi et al. | |
| 2001/0001006 | A1 * | 5/2001 | Jiang et al. | 372/99 |
| 2005/0194523 | A1 * | 9/2005 | VanWiggeren et al. | 250/225 |
| 2006/0034729 | A1 * | 2/2006 | Poponin | 422/82.05 |

(Continued)

FOREIGN PATENT DOCUMENTS

| JP | | 4-168330 A | 6/1992 | |
| JP | WO 2006/135097 | | * 12/2006 | ............. G01N 21/27 |

(Continued)

OTHER PUBLICATIONS

Barnes (2003) Nature 424: 824-830.*
Hibbins et al. "Resonant absorption of electromagnetic fields by surface plasmons buried in a multi layered plasmonic nanostructure"; Physical Review B; Aug. 15, 2006; vol. 74; NR 7; pp. 73408-1-73408-4.*

(Continued)

*Primary Examiner* — Chris L Chin
*Assistant Examiner* — Richard Moerschell
(74) *Attorney, Agent, or Firm* — Fitzpatrick, Cella, Harper & Scinto

(57) ABSTRACT

A chemical sensor element contains a resonator having a first reflector in which particles of a fine metal structure are arranged two-dimensionally and periodically is counterposed with interposition of a dielectric layer to a second reflector, wherein the resonance wavelength of a resonator in which the entire of the first reflector is replaced by a metal thin film having the same thickness as the metal fine structure is different from the surface plasmon resonance wavelength induced in the metal fine structure; and the mode of the surface plasmon resonance excited in the metal fine structure is coupled with the mode of the resonator in which the entire of the first reflector is replaced by the metal thin film.

8 Claims, 8 Drawing Sheets

(56) References Cited

U.S. PATENT DOCUMENTS

| | | |
|---|---|---|
| 2007/0206194 A1 | 9/2007 | Yamada et al. |
| 2007/0263221 A1 | 11/2007 | Naya et al. |
| 2008/0246970 A1 | 10/2008 | Kuroda et al. |
| 2009/0109422 A1 | 4/2009 | Handa et al. |
| 2009/0117669 A1 | 5/2009 | Yamamichi et al. |
| 2009/0128822 A1 | 5/2009 | Yamamichi et al. |

FOREIGN PATENT DOCUMENTS

| | | |
|---|---|---|
| JP | 2007-538264 A | 12/2007 |
| WO | 2005/114298 A2 | 12/2005 |
| WO | 2006/135097 A1 | 12/2006 |

OTHER PUBLICATIONS

Amanda J. Haes et al., "A Localized Surface Plasmon Resonance Biosensor: First Steps Toward an Assay for Alzheimer's Disease," NANO Letters 2004, vol. 4, No. 6, 1029-1034.

A. P. Hibbins et al., "Resonant Absorption of Electromagnetic Fields by Surface Plasmons Buried in a Multilayered Plasmonic Nanostructure," Physical Review B 74, 073408 (2006).

Klaus M. Engenhardt et al., "Surface-plasmon-polariton Excitation of Optical Microcavities and Second-harmonic Emission," 17(4) J. Opt. Soc. Am. B 593-599 (Apr. 2000).

Jelena Vuckovic et al., "Surface plasmon enhanced LED," QELS 2000, Technical Digest May 7-12, pp. 41-42 (2000).

* cited by examiner

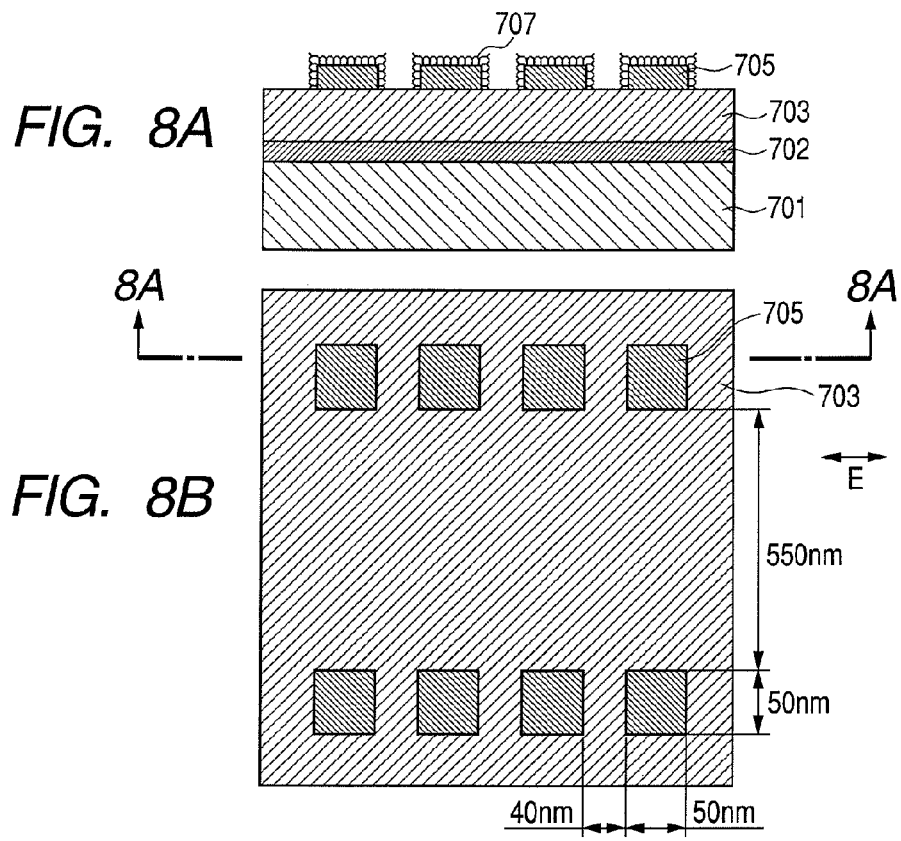
FIG. 8A
FIG. 8B
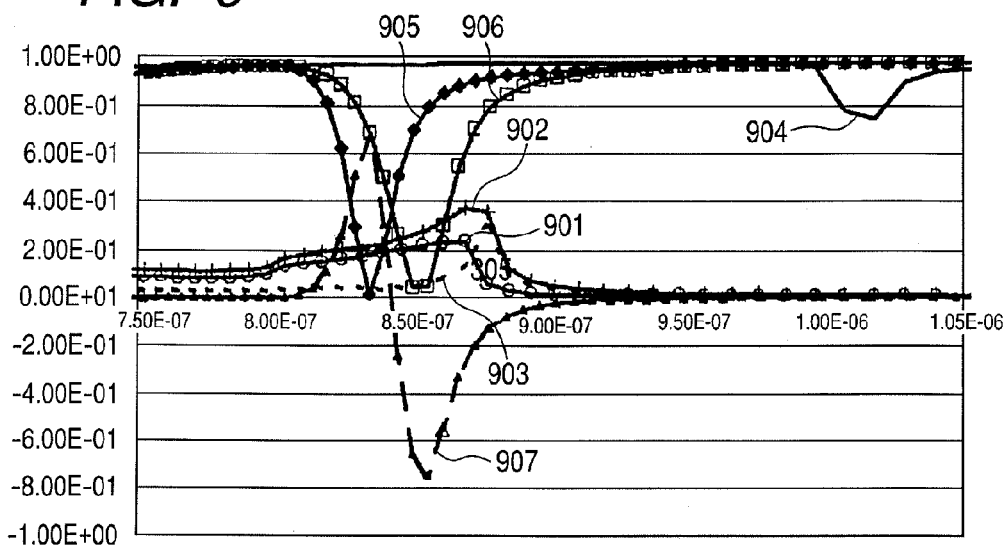
FIG. 9

CHEMICAL SENSOR ELEMENT, SENSING APPARATUS, AND SENSING METHOD

TECHNICAL FIELD

The present invention relates to a chemical sensor, particularly to a chemical sensor for detecting, from a change in an optical spectrum, a change in a dielectric constant caused by an antigen-antibody reaction on the surface of the sensor element. The present invention relates also to a sensing apparatus and sensing method employing the sensor.

BACKGROUND ART

A localized surface plasmon resonance (LSPR) can be induced in an electroconductive fine structure. Resonance conditions of the LSPR depend on the refractive index and dielectric constant surrounding the electroconductive structure. Therefore, a change in the dielectric constant around the electroconductive structure can be detected by a change in the resonance conditions. The change in the resonance conditions can be detected by measuring a change in the optical spectrum of the light beam projected to and transmitted through the electroconductive structure.

The LSPR is sensitive to a change in the refractive index and dielectric constant of the medium surrounding the electroconductive structure, and is applicable to high-sensitive detection of a refractive index.

As shown below, when a biological reaction causes a change in the dielectric constant, this change can be utilized for a high-sensitive bio-sensing. Therefore, the LSPR is promising in broad application fields including medical treatment, foodstuffs, and environment.

For example, occurrence of an antigen-antibody reaction around the electroconductive structure can be detected by utilizing the LSPR. Richard P. Van Duyne et al. (NANO LETTERS 2004, vol. 4, No. 6, 1029-1034) discloses a silver microparticulate thin layer structure formed as an electroconductive structure on a smooth base plate. With this structure, the antigen concentration is determined from a change in the optical spectrum between a state of antibody adhesion and a state of additional adhesion of antigen around a silver microparticulate thin film structure.

In other examples, enzyme-substrate complex formation, complementary base pair formation by DNA hybridization, and so forth can be detected similarly.

U.S. Patent Application Publication No. 2007/0263221 discloses a sensor, which has a first reflector, a translucent body, and a second reflector placed in the named order from the measurement light-input side. In this sensor, the light beam introduced through the first reflector into the translucent body is repeatedly reflected between the first reflector and the second reflector to cause multiple reflection and multiple interference. Adhesion of a sample to the sensor changes the absorption peak spectrum by the multiple interference, enabling analysis of the sample. In addition to the above absorption peak spectrum given by the multiple interference, an absorption peak is developed by the localized surface plasmon resonance, and this change in the absorption peak spectrum enables analysis of the sample. U.S. Patent Application Publication No. 2007/0263221 describes a structure of the first reflector having fine holes and a structure having metal fine particles, as the first reflector.

The above prior art techniques are not sufficient in the measurement sensitivity for high-sensitive detection of a low concentration of a target substance.

For high-sensitive detection of a target substance, it is necessary to increase the wavelength shift of the resonance spectrum by adhesion of the target substance and to decrease the width of the resonance spectrum. For example, in detection of a target substance adhesion by difference of the spectra caused by a reaction, a small width of the resonance spectrum and large shift of the wavelength will increase the differential of the spectrum by the reaction to enable high-sensitive detection. For this purpose, U.S. Patent Application Publication No. 2007/0263221 proposes a structure which has a metal hole-array structure or a metal microparticulate arrangement structure as the reflector of the resonator. However, the proposed structures do not achieve any of the effects of decrease of the width of the resonance spectrum and increase of the shift of the resonance spectrum.

DISCLOSURE OF THE INVENTION

The present invention intends to solve the above-mentioned problems, and intends to provide a chemical sensor element having a resonator construction which enables decrease of the width of the resonance spectrum and increase of the shift of the resonance spectrum for high-sensitive measurement.

The present invention is directed to a chemical sensor element containing a resonator having a first reflector in which particles of a fine metal structure are arranged two-dimensionally and periodically is counterposed with interposition of a dielectric layer to a second reflector:

wherein the resonance wavelength of a resonator in which the entire of the first reflector is replaced by a metal thin film having the same thickness as the metal fine structure is different from the surface plasmon resonance wavelength induced in the metal fine structure; and the mode of the surface plasmon resonance excited in the metal fine structure is coupled with the mode of the resonator in which the entire of the first reflector is replaced by the metal thin film.

The resonance wavelength of the resonator in which the entire of the first reflector is replaced by the metal thin film can be within ±25% of the plasmon resonance wavelength.

The resonance wavelength $\lambda_1$ of the resonator can be represented by the equation:

$$m\lambda_1 = 2nL + (\phi_1/2\pi)\lambda_1 + (\phi_2/2\pi)\lambda_1$$

wherein n is the refractive index of the dielectric layer and L is the thickness of the dielectric layer, $\lambda_1$ is the resonance wavelength of the resonator in which the entire of the first reflector is replaced by the metal thin film, $\phi_1$ is a change of phase caused by reflection of the light propagating in the dielectric layer by the metal thin film, $\phi_2$ is the change of phase caused by reflection of the light propagating in the dielectric layer by the second reflector, and m is a natural number.

The second reflector can be comprised of a metal.

The metal fine structure or the second reflector can be comprised of any one selected from the group consisting of gold, silver, copper, platinum and aluminum.

The particle of the metal fine structure can be in a shape of a rectangular solid, a polygonal column, or a round column.

The particles of the metal fine structure can be arranged in triangular lattice.

The product of the arrangement pitch of the metal fine structure and the refractive index of the dielectric layer or the refractive index of the medium surrounding the metal fine structure can be equal to the wavelength of the plasmon resonance induced in the metal fine structure.

The present invention is directed to a sensing apparatus, comprising:

the chemical sensor element,
a light source for projecting a light beam perpendicularly to a face of the resonator constituting the chemical sensor element on which the metal fine structure is formed, and
a light detecting element for detecting reflected light from the chemical sensor element.

The apparatus further can comprise an optical element for converting the light projected to the chemical sensor element into linear polarized light, and the direction of an electric field vector of the linear polarized light from the optical element can be coincide with the short-pitch direction of an arrangement of the metal fine structure.

The present invention is directed to a sensing method for detecting a target substance by employing the chemical sensor element, comprising:

a first step of detecting a light beam projected to and reflected by the chemical sensor element in the absence of the target substance adhering to the chemical sensor element,
a second step of detecting a light beam projected to and reflected by the chemical sensor element in the presence of the target substance adhering to the chemical sensor element, and
a third step of calculating a differential between the optical spectrum of the reflected light detected in the first step and the optical spectrum of the reflected light detected in the second step.

The present invention couples the surface plasmon resonance mode which increases the spectrum shift caused by a reaction, and the resonator mode which decreases the width of the spectrum. Thereby the resulting spectrum has the characteristics of the both modes to give a small width of the spectrum. The chemical sensor of the present invention enables high-sensitive measurement in comparison with that of prior art techniques by decreasing the width of the resonance spectrum and by increasing the shift of the resonance spectrum.

Further features of the present invention will become apparent from the following description of exemplary embodiments with reference to the attached drawings.

BRIEF DESCRIPTION OF THE DRAWINGS

FIG. 8A is a sectional view of a constitution of a sensor element of Example 2 of the present invention.

FIG. 8B is a plan view of a constitution of a sensor element of Example 2 of the present invention.

FIG. 9 is a characteristic diagram showing reflection spectra given by a sensor element of Example 1 of the present invention formed on a simple quartz plate.

BEST MODE FOR CARRYING OUT THE INVENTION

Embodiments of the present invention are described below with reference to drawings.

The sensor element of the present invention determines a concentration of a target substance from a change in the optical spectrum caused by adhesion of a target substance on the surface of the sensor element. Therefore, for high-sensitive sensing, it is important to detect sensitively an optical spectrum change caused by adhesion of a target substance onto the element surface. For the high-sensitive sensing, the optical spectrum should have a narrow spectral peak and a large shift of the spectral peak caused by adhesion of the target substance.

Figure 1A:
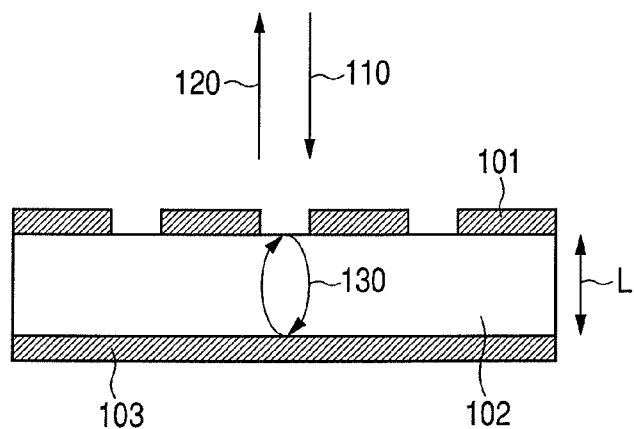
FIG. 1A is a sectional view of a resonator structure of a sensor element of the present invention.

FIG. 1A is a sectional view of a resonator structure of a sensor element of an embodiment of the present invention. In FIG. 1A, particles of metal fine structure 101 are arranged two-dimensionally and periodically on dielectric layer 102 formed on reflector 103.

Incident light beam 110 introduced to metal fine structure 101 induces local surface plasmon resonance (LSPR) in metal fine structure 101 to increase the reflectivity of metal fine structure 101. This metal fine structure 101 serves as a reflection mirror (first reflector) having wavelength dependency of the reflectivity. Reflected light beam 120 is formed by reflection of incident light beam 110 by metal fine structure 101.

The LSPR is a collective vibration mode of free electrons induced in a metal fine structure (metal fine particles). The resonance wavelength of the LSPR depends on the dielectric constant of the metal itself and the dielectric constant of the dielectric material in contact with the metal. The LSPR is induced in metal fine particles smaller than the wavelength of the projected light beam according to the boundary conditions at the metal fine particle surface. The resonance conditions are sensitive to the dielectric constant of the dielectric material in contact with the metal particles. Therefore the resonance wavelength is changed by adhesion of a target substance on the surface of the metal fine particles.

A part of the introduced light beam penetrates through metal fine structure 101 (first reflector) to a resonator constituted of metal fine structure 101 (first reflector), dielectric layer 102 and reflector 103 (second reflector) to cause resonance as indicated by reference numeral 130. That is, the chemical sensor element of this embodiment is regarded to be constituted of a Fabry-Prot type resonator in which mirror of the one side is a metal fine structure capable of inducing the LSPR.

The LSPR causes a large shift of the spectrum by a reaction on the surface of the metal fine structure. On the other hand, the mode of a Fabry-Perot resonator gives a spectrum of a small width. The chemical sensor of this embodiment is characterized by coupling of the LSPR mode with the Fabry-Perot resonator mode to obtain a spectrum having the both characteristics.

In the resonator structure disclosed in U.S. Patent Application Publication No. 2007-0263221, neither the resonance wavelength of the resonator structure nor the resonance wavelength of the LSPR of the metal fine particles are not considered at all. Therefore, the above two modes are not coupled in the disclosed resonator structure.

The coupling of the LSPR mode of the metal fine structure with Fabry-Perot resonator mode formed by reflecting function of the metal fine structure is described below. The Fabry-Perot resonator mode herein signifies a resonance mode of the resonator in which the entire of the first reflector constituted of the metal fine structure is replaced by a metal thin film having the same thickness as the metal fine structure. However, actually in the present invention, the metal fine structure itself excites both the LSPR mode and the resonance mode of the entire element as the resonator to couple the two modes. Therefore, the description below is conceptional.

Figure 1B:
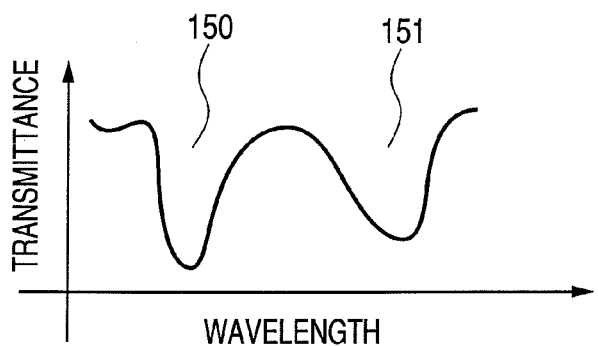
FIG. 1B shows a characteristic transmission spectrum without coupling of a plasmon resonance mode with a Fabry-Perot resonator mode.

When the LSPR mode of the metal fine structure is not coupled with the Fabry-Perot resonator mode, the two modes are independent respectively. In such a case, the spectrum of the transmitted light is like that shown in FIG. 1B. In FIG. 1B, the ordinate denotes the transmittance and the abscissa denotes the wavelength. In this transmitted light spectrum, spectrum 150 of LSPR of the metal fine structure and spectrum 151 of the resonator mode are separated independently.

Figure 1C:
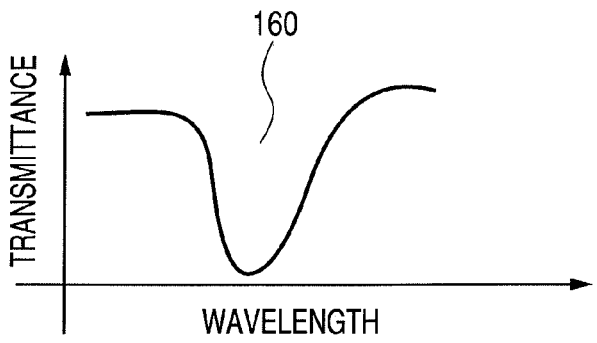
FIG. 1C shows a characteristic transmission spectrum with coupling of a plasmon resonance mode with a Fabry-Perot resonator mode.

On the other hand, when the two modes are coupled, the spectrum is like that shown in FIG. 1C. In FIG. 1C, the ordinate denotes the transmittance and the abscissa denotes the wavelength. In this transmitted light spectrum, the two spectra are united into one coupling mode spectrum 160.

Next, guidance for design for coupling of the LSPR spectrum of the metal fine structure with the resonator mode is described below.

The mode of the LSPR is formed by collective motion of free electrons in the metal fine structure. Therefore, in the resonance, vibrating surface charges are generated on the surface of metal fine structure, so that the electric field amplitude cannot be zero on the surface of the metal fine structure: no loop of a standing wave can be formed on the surface. On the other hand, in the mode of Fabry-Perot resonator, the metal fine structure is a part of a mirror constituting an end face as the reflector of the Fabry-Perot resonator, forming a node of a standing wave in the resonator. Therefore, if the metal fine structure is placed at the position of the node of the Fabry-Perot resonator, the LSPR of the metal fine structure cannot be excited. Therefore, the metal fine structure is preferably deviated slightly from the position of the node of the resonator mode.

However, when the positional deviation from the node position is excessively large, even if the LSPR can be excited, the mode of the Fabry-Perot resonator cannot be excited at the same wavelength.

The sensor element of this embodiment is constituted such that the resonance wavelength $\lambda_1$ of the mode of the Fabry-Perot resonator having a metal thin film of the same thickness as metal fine structure 100 does not precisely equal to the resonance wavelength $\lambda_0$ of metal fine structure 101, but approximate to the resonance wavelength $\lambda_0$, Specifically, the wavelength $\lambda_1$ of the resonance of a mode of the Fabry-Perot resonator having a metal thin film of the same thickness as the metal fine structure 101 is preferably within the spectrum line width of the plasmon resonance spectrum induced in metal fine structure 101.

Figure 2:
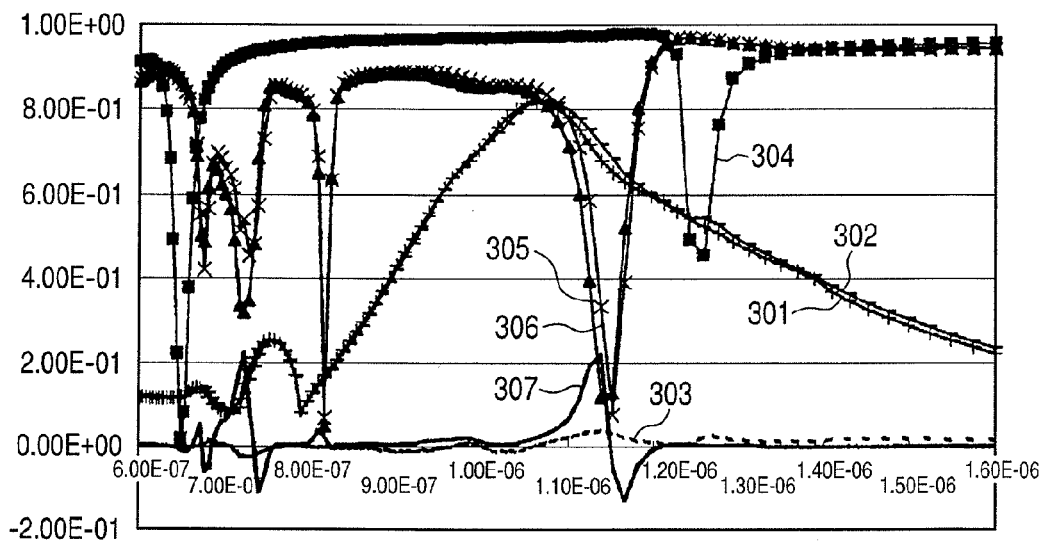
FIG. 2 shows typical characteristic spectra of plasmon resonance cause by a metal fine structure.

The typical spectra of the plasmon resonance in the metal fine structure are shown in FIG. 2. The ordinate denotes the transmittance, and the abscissa denotes the wavelength. In FIG. 2, the reference numerals 301 and 302 indicate typical spectra of the plasmon resonance. For example, the wavelength range of the line width of the spectrum indicated by numeral 301 ranges from 900 nm (−15.9%) to 1300 nm (21.5%) with the resonance wavelength 1070 nm at the center. The line width of the plasmon resonance is generally within the range of ±25% of the resonance wavelength. Therefore, in the chemical sensor of the present invention also, the resonance wavelength $\lambda_1$ in the Fabry-Perot resonator is preferably within ±25% around the resonance wavelength $\lambda_0$ in the metal fine structure.

Next, the setting of the relation of parameters such as the resonance wavelength $\lambda_1$ with the resonator length is described below.

The resonance wavelength $\lambda_1$ of the Fabry-Perot resonator which is produced by replacing the metal fine structure of the resonator of a sensor element of this embodiment by a metal thin film having the same thickness as the metal fine structure satisfies Equation 1 below.

$$m\lambda_1 = 2nL + (\phi_2/2\pi)\lambda_1 + (\phi_2/2\pi)\lambda_1 \quad \text{(Equation 1)}$$

In Equation 1, the symbols denote the followings: L, the thickness of dielectric layer 102; n, the refractive index of dielectric layer 102; m, a natural number; $\lambda_1$, wavelength of light resonating in the resonator; $\phi_2$, the phase change of light caused by reflection by the metal thin film having the same thickness as metal fine structure 101 in the dielectric layer; $\phi_2$, the phase change of light caused by reflection by the reflector. Incidentally, the phase change of perpendicular incident light caused by reflection by a medium having a finite loss is represented by Equation 2 below:

$$\tan \phi = (2n_1 k_2)/(n_1^2 + n_2^2 + k_2^2) \quad \text{(Equation 2)}$$

In Equation 2, the symbols denote the followings: $\phi$, the phase change of perpendicular incident light caused by reflection by a medium having a finite loss; $n_1$, the refractive index of the medium at the incident side; $n_2$, the refractive index of the medium having a finite loss; $k_2$, the extinction coefficient of the medium having a finite loss.

In Equation 1, the first term shows the condition that the thickness L of dielectric layer 102 is integral multiple of the half-wave length of the light in the resonator. The second term shows the phase change at reflection of the light by the metal thin film in the resonator. The third term shows the phase change at reflection of the light by the reflector in the resonator.

The effective resonator length of the Fabry-Perot resonator is not a simple product (=nL) of the thickness L of dielectric layer 102 and the refractive index n thereof, but includes optical path lengths corresponding to the phase change by reflection and transmission at the metal thin film and at the reflector 103. Therefore, the effective resonator length of the resonator construction of this embodiment is also not a simple value of nL, but is an effective optical path length including phase delay by the reflection and transmission at metal fine structure 101 and reflector 103 in opposition. The optical path length is a sum of an optical distance corresponding to the phase changes at reflection by metal fine structure 101 and reflector 103 and an optical distance corresponding to the product of thickness L of dielectric layer 102 and the refractive index thereof. The phase change by the reflection can be derived from optical constants of the respective mediums from measurement of the reflectivity spectrum or a like measurement.

As described above, the spectrum of the resonator mode can be obtained at a desired wavelength by adjusting the thickness L of dielectric layer 102 according to the above Equation 1. In other words, the LSPR mode of metal fine structure 101 and the resonator mode can be coupled by adjusting the thickness L of dielectric layer 102. Thereby the spectrum peak width can be decreased and the shift of the spectrum peak caused by adhesion of a sample can be increased for high-sensitive sensing.

On the other hand, the metal fine structure can be designed by deciding the phase change at the transmission and reflection. However, generally the phase change at the transmission and reflection at the metal fine structure cannot readily be estimated, and the wavelength dispersion characteristics of the metal fine structure should also be considered.

Further, the metal fine structure, incorporated into the resonator structure is coupled with the resonator mode to change the resonance wavelength depending on the strength of the coupling of the resonator and the metal fine structure. Therefore, the sensor element can be designed simply and suitably by utilizing the relation between the plasmon resonance wavelength $\lambda 0$ of the metal fine structure and the resonance wavelength $\lambda 1$ of the resonator structure having a metal thin film having the same thickness of the film as the metal fine structure.

Not only with the LSPR mode of metal fine structure 101, the resonator mode is preferably coupled with another optical mode of metal fine structure 101. For example, the resonator mode may be coupled with a mode of diffracted light propagation parallel to the element surface, like Wood's anomaly, to decrease further the resonance spectrum line width. A constitution utilizing the Wood's anomaly is descried later in detail in Example.

Basically, the resonance wavelength of the sensor element designed as above of this embodiment tends to appear between the resonance wavelength of the metal fine structure and the resonance wavelength of the resonator mode. However, when the coupling of the modes includes another mode such as Wood's anomaly in addition to the resonator mode and the resonance mode of the metal fine structure, the resonance wavelength of the sensor element appears between the shortest wavelength and the longest wavelength of the resonance wavelengths of the modes The constitution of the chemical sensor of the present invention is described specifically below.

Figure 3A:
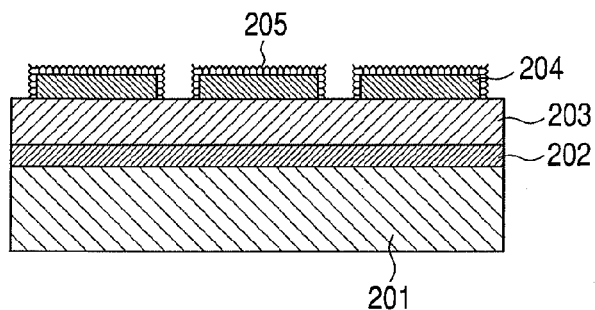
FIG. 3A is a schematic sectional view of a constitution of a chemical sensor of the present invention taken along line 3A-3A in FIG. 3B.
Figure 3B:
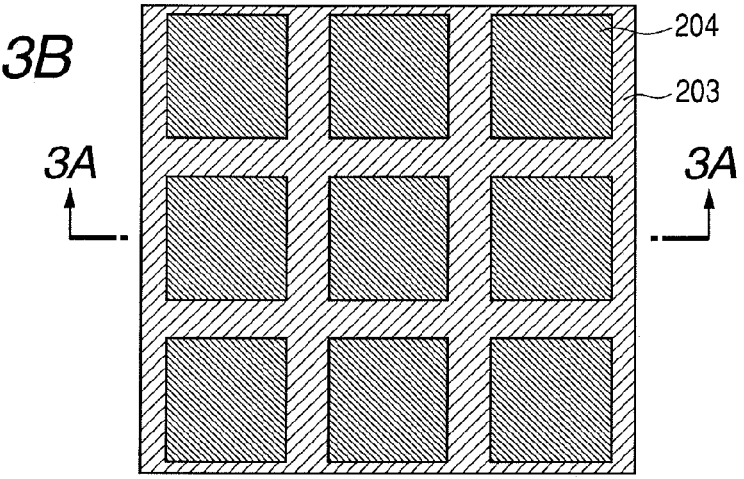
FIG. 3B is a schematic plan view of constitution of a chemical sensor of the present invention.

FIGS. 3A and 3B illustrate specifically a constitution of a chemical sensor element of an embodiment of the present invention: FIG. 3A is a sectional view taken along the line 3A-3A in FIG. 3B, a plan view.

Reflector plate 202 is formed on a base plate 201, and thereon dielectric layer 203 is provided. Dielectric layer 203 is a quartz layer having a refractive index at 1.46. On the surface of dielectric layer 203, particles of metal fine structure 204 are formed.

The particle of metal fine structure 204 is rectangular in shape, having the lengthwise and crosswise sizes of 270 nm and a thickness of 40 nm. The particles of metal fine structure 204 are arranged periodically in a square lattice in an arrangement pitch of 540 nm. The shape of particles of metal fine structure 204 is not limited to the rectangular solid but may be cylindrical or polygonal-columnar.

The material of metal fine structure 204 is gold generally, but is not limited thereto and any material may be selected which is capable of inducing the localized plasmon resonance: the preferred materials include metals having low imaginary part of dielectric constant such as Ag, Pt, Cu, Al, and alloys and mixtures thereof.

In this embodiment, the metal fine structure particles are arranged periodically in a square lattice, but may be in other periodical arrangement such as a triangular lattice. The triangular lattice arrangement decreases the dependency on the incident angle. In this embodiment, the surface of the metal fine structure 204 is modified by antibody 205.

Reflector plate 202 may be a metal mirror, a multilayered dielectric mirror having high-refractive layers and low-refractive layers laminated alternately, or a like mirror. A metal mirror as reflector plate 202 enables a broad wavelength band range with a high reflectivity, whereas a multilayered dielectric mirror used as reflector plate 202 realizes a reflector of high reflectivity since the multilayered dielectric mirror has a low reflectivity.

In the case where metal fine structure 204 is formed on a quartz base plate without reflector plate 202 and is surrounded by water, reflectivity spectrum 301 as shown in FIG. 2 is obtained.

Reflectivity spectrum 301 shows increase of the reflectivity by induction of localized plasmon resonance (LSPR) in metal fine structure 204. Thus metal fine structure 204 functions as a reflection mirror having a wavelength-dependent reflectivity.

As described above, LSPR is a collective vibration mode of free electrons induced in the metal fine particles. The resonance wavelength of the LSPR depends on the dielectric constant of the metal itself and the dielectric constant of the dielectric substance in contact with the metal. The conditions of the resonance are sensitive to the dielectric constant of the dielectric material in contact with the metal. For example, adhesion of a target substance to the surface of metal fine particle structure 204 will cause a change in the resonance wavelength of the LSPR. Consequently, the reflectivity spectrum 301 is changed to reflectivity spectrum 302 as shown in FIG. 2. This means that at a certain wavelength, the reflectivity is changed by the adhesion of a target substance. The difference between reflectivity spectrum 302 and reflectivity 301 is shown as differential spectrum 303 in FIG. 2.

Thus the sensor element of this embodiment has a constitution of a Fabry-Perot resonator which has metal fine structure 204 as the mirror at one side of the resonator. Adhesion of a target substance on the surface of metal fine structure 204 changes the reflectivity spectrum by LSPR of metal fine structure 204. This spectrum change causes a change in conditions of the resonator mode of the sensor element, causing a shift of the peak of the reflectivity spectrum. This shift is utilized for sensing of a chemical substance.

In FIG. 2, reflectivity spectrum 305 shows the reflectivity of the sensor element of this embodiment before adhesion of the target substance, and reflectivity spectrum 306 shows the reflectivity after the adhesion. The change in the optical spectrum by the target substance adhesion calculated by subtracting reflectivity spectrum 305 from reflectivity spectrum 306 is shown as differential spectrum 307.

Separate metal fine structure 204 gives differential spectrum 303 by adhesion of the target substance with maximum differential value of about 0.02 as shown in FIG. 2. In contrast, the sensor element construction of this embodiment in which metal fine structure 204 constitutes one end face of the resonator gives the differential spectrum 307 having a maximum of about 0.2. Thus the change in the optical spectrum by adhesion of the target substance is improved by a factor of about 10, by numerical calculation.

As described above, the sensor element of this embodiment has a resonator mode and an LSPR mode, and gives an optical spectrum having characteristics of LSPR and the resonator by coupling of the two modes.

Example 1

A sensor of Example 1 of the present invention is described below.

Firstly, a process for production of the sensor element of the present invention is described. FIGS. 4A-4D illustrate steps of production of the sensor element of this Example.

A quartz plate is used as the base plate 401, having a thickness of 525 μm. The thickness of quartz base plate 401 is not limited thereto.

Figure 4A:
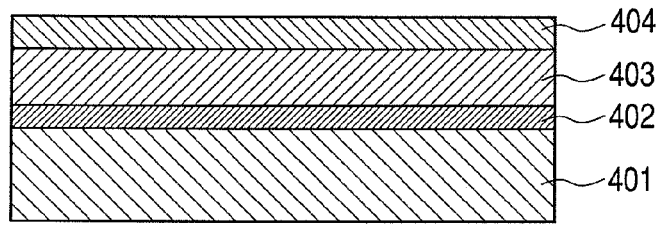
FIG. 4 illustrates steps of production of the sensor element of Example 1 of the present invention.

As illustrated in FIG. 4A, a Au thin film is formed, on quartz base plate 401, as metal layer 402 in a thickness of about 100 nm by vapor deposition. The material of metal layer 402 is not limited to Au, but may be any metal which has a high reflectivity in the measurement wavelength range of the sensor element of this Example. Specifically, the material of metal layer 402 includes gold, silver, copper, platinum, and aluminum. The method of film formation is not limited to vapor deposition, but may be sputtering.

On the formed metal layer 402, a silicon dioxide film is formed as resonator layer 403 in a thickness of about 380 nm. The material of resonator layer 403 is not limited to silicon dioxide, but may be any material which has a high transmittance in the range of measurement with the sensor of this Example. The method of the film formation is not limited to sputtering, but includes CVD and SOG for the formation of resonator layer 403.

Figure 4B:
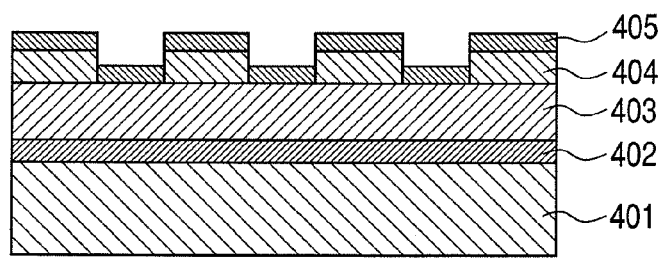

On resonator layer 403, EB resist layer 404 is formed. EB resist layer 404 is patterned in a shape of squares having sides of 270 nm by means of an electron beam drawing apparatus as illustrated in FIG. 4B. After the patterning, EB resist layer 404 is developed. After the development, on the face having EB resist layer 404, a metal thin film 405 is formed in a thickness of about 40 nm by vapor deposition. Finally, the element base plate is immersed in an EB resist solvent to obtain sensor element 406 by a lift-off method as illustrated in FIG. 4C.

In the above production process, metal fine structure 405 is patterned by an electron beam drawing apparatus, but is not limited thereto. Metal fine structure 405 may be patterned by a photolithography apparatus, or an FIB (focused ion beam) working apparatus.

Figure 4C:
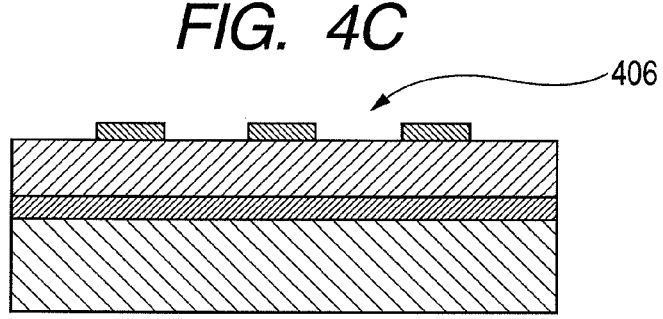

Through the steps illustrated in FIGS. 4A to 4C, metal fine structure 405 having a thickness of 40 nm, one side length of 270 nm is formed in which the particles of metal fine structure 405 are arranged periodically in a square lattice at an arrangement pitch of 540 nm.

Of the sensor element produced as described above, the surface of metal fine structure 405 is modified with an antibody. An example of the antibody is anti-AFP antibody (anti-α-fetoprotein antibody). This anti-AFP antibody is immobilized on the surface of metal fine structure 405, and thereon an ethanol solution of 11-mercaptoundecanoic acid, which has a thiol group, is dropped by a spotter or the like to give a bared carboxyl group to the surface of metal fine structure 405.

Subsequently, an aqueous solution of N-hydroxysulfosuccinimide and an aqueous solution of 1-ethyl-3-[3-dimethylamino]propyl carbodiimide hydrochloride are dropped by a spotter or the like onto the reaction region to give a bared succinimide group onto the surface of metal fine structure 405.

Figure 4D:
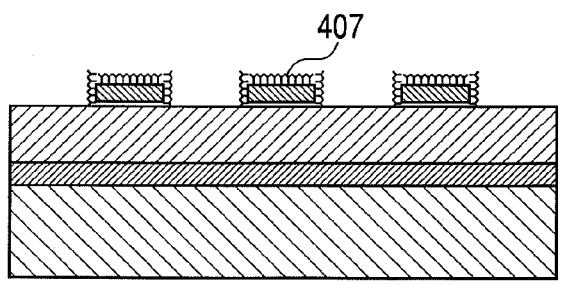

Further, streptoavidin is allowed to react to modify the surface of metal fine structure 405. Onto this metal fine structure 405, a biotin-containing anti-AFP antibody is immobilized. Thereby, metal fine structure 405 is modified by antibody 407 as illustrated in FIG. 4D.

Next, an antigen-antibody reaction on sensor element 406 prepared above and optical spectrum measurement employing the sensor are described below.

Figure 5A:
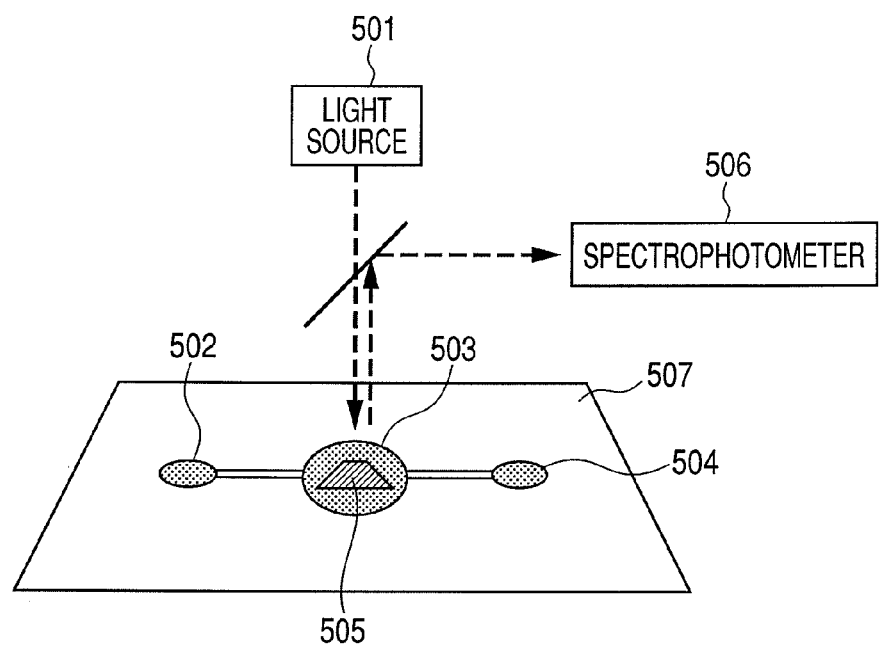
FIG. 5A is a block diagram illustrating a system for conducting an antigen-antibody reaction and an optical spectrum measurement.

The antigen-antibody reaction and the optical spectrum measurement are conducted with a system employing a measurement board 507 illustrated in FIG. 5A. Measurement board 507 has a reaction well 503 containing sensor element 505, and inlet 502 and outlet 504 communicating to reaction well 503. Light source 501 is placed above reaction well 503. The light beam from light source 501 is reflected by sensor element 505. The reflected light beam is introduced through a mirror to spectrophotometer 506.

In the measurement, an analyte containing AFP is introduced through inlet 502. In reaction well 503, AFP is trapped by sensor element 505. The analyte is discharged from outlet 504. Then a phosphate buffer solution is poured through inlet 502 to wash and fill the inside of reaction well 503.

For measurement of optical spectrum of sensor element 505, a light beam is projected from light source 501 to sensor element 505, and the reflected light from sensor element 505 is subjected to spectral measurement with spectrophotometer 506.

Figure 5B:
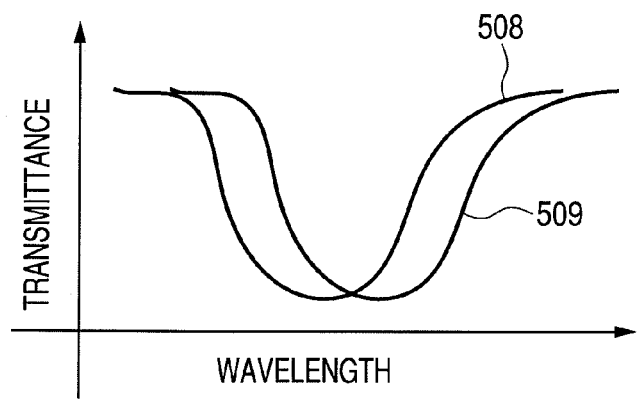
FIG. 5B is a characteristic diagram showing optical spectra taken by the system illustrated in FIG. 5A.

FIG. 5B shows the optical spectrum derived by the above system. The ordinate indicates the transmittance, and the abscissa indicates the wavelength. In FIG. 5B, curve 508 shows the optical spectrum taken before the antigen-antibody reaction, and curve 509 shows the optical spectrum after the antigen-antibody reaction. The spectral change by the reaction is derived by comparison of optical spectra 508, 509. From this change, the concentration of the target substance is estimated. For estimation of the target substance in the analyte, the relation between the spectrum change and the concentration is derived preliminarily by use of AFP solutions of known concentrations.

Figure 6:
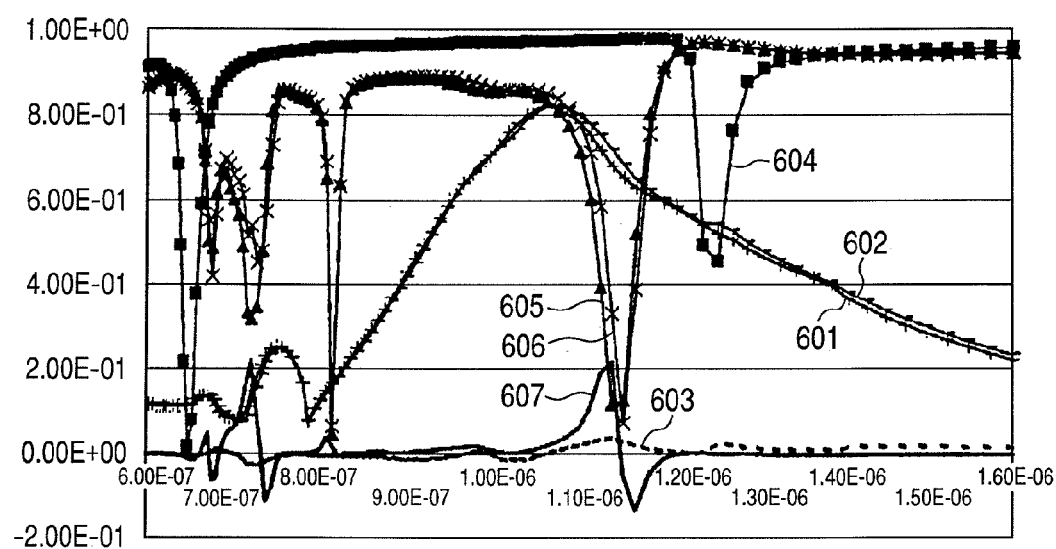
FIG. 6 is a characteristic diagram showing reflection spectra obtained by a sensor element of Example 1 of the present invention formed on a simple quartz plate.

FIG. 6 shows reflection spectra from metal fine structure 405 formed on a simple quartz base plate. In FIG. 6, the ordinate indicates the reflectivity, and the abscissa indicates the wavelength. Curve 601 shows the reflection spectrum before adhesion of the target substance, and curve 602 shows the reflection spectrum after adhesion of the target substance. The change of the reflectivity spectrum by the target substance adhesion is calculated by subtracting the reflectivity spectrum after the adhesion from the reflectivity spectrum before the reaction, and is shown as differential spectrum 603.

From the reflection spectra shown in FIG. 6, the resonance wavelength in metal fine structure 405 is estimated to be about 1050 nm by assuming that metal fine structure 405 is surrounded by water. In this Example, the resonance wavelength of the sensor element appears at about 1150 nm, being deviated to the longer wavelength side by about 10% relative to the resonance wavelength of metal fine structure 405.

Considering the phase change at reflection on the end faces of the resonator, at the thickness of resonator 403 of about 380 nm, the effective resonator of the resonator is 630 nm. In this case, the resonance wavelength in resonator layer 403 is about 1260 nm (reflection spectrum 604). With this constitution, the resonance mode (resonance wavelength: 1260 nm) of the resonator and the LSPR resonance (resonance wavelength: 1050 nm) are coupled together to give the resonance wavelength of the sensor element at about 1150 nm between the two resonance wavelengths.

For the above reason, the resonator layer 403 is formed in a thickness of 380 nm in the above-mentioned element production process. The sensor element of this Example produced above gives reflection spectrum 605 before adhesion of the target substance, and reflection spectrum 606 after adhesion of the target substance. The change of the reflection spectrum caused by adhesion of the target substance is differential spectrum 607.

From the above result, the sensor element of this Example gives maximum differential of 0.2, showing improvement of the sensing sensitivity in comparison with the sensitivity of the metal fine particles (maximum differential: about 0.02.).

In this Example, the resonance wavelength of the sensor element is 1150 nm, but is not limited thereto. For example, the resonance wavelength of the sensor element may be set at a shorter wavelength side of the resonance wavelength 1050 nm of metal fine structure 405.

The constitution of metal fine structure 405 is not limited to the illustrated one.

Further, the reflectivity around the resonance wavelength of LSPR of metal fine structure 405 is preferably set such that the peak is deep and sharp in constituting the resonator construction by the sensor element of the present invention.

The respective metal fine particles constituting metal fine structure 405 are not limited to be rectangular, but may be polygonal-columnar or cylindrical. With increase of degree of symmetry of the metal fine particles, the dependency of the element on the light polarization is decreased. The arrangement of the metal fine particles is not limited to be in a square lattice, but may be in a triangular or hexagonal lattice for decrease of the dependency on light polarization of the element.

The sensor element of the present invention, in which the mode of the metal fine structure and the mode of the resonator combined thereto are coupled together, has a simple element constitution for high-sensitive sensing, and can be produced readily.

Example 2

A sensor element of Example 2 of the present invention is described below.

Firstly, a process for producing the sensor element of this Example is described. FIGS. 7A to 7D illustrate the sequence of the steps of production of the sensor element of this Example.

Quartz base plate 701 is provided, having a thickness of 525 μm. The thickness of quartz base plate 701 is not limited thereto.

Figure 7A:
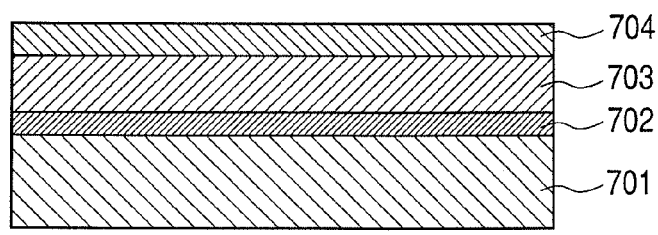
FIGS. 7A, 7B, 7C and 7D illustrate steps of production of the sensor element of Example 2 of the present invention.
Figure 7B:
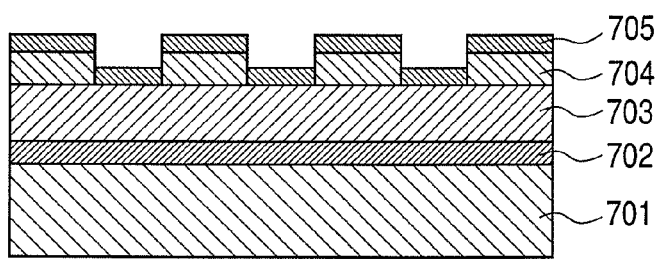

As illustrated in FIG. 7A, on the surface of quartz base plate 701, a Au thin film is formed as metal layer 702 in a thickness of about 100 nm by vapor deposition. The material of metal layer 702 is not limited to Au, but may be any metal which has a high reflectivity in the measurement wavelength range of the sensor element of this Example. Specifically, the material of metal layer 702 includes gold, silver, copper, platinum, and aluminum. The method of formation of metal film 702 is not limited to vapor deposition, but may be sputtering.

On the formed metal layer 702, a silicon dioxide film is formed as resonator layer 703 in a thickness of about 300 nm. The material of resonator layer 703 is not limited to silicon dioxide, but may be any material which has a high transmittance in the range of measurement with the sensor of this Example. The method for formation of the resonator layer 703 film is not limited to sputtering, but includes CVD and SOG for the formation of resonator layer 703.

On resonator layer 703, EB resist layer 704 is formed. EB resist layer 704 is patterned to have squares having sides of 50 nm by means of an electron beam drawing apparatus. After the patterning, EB resist layer 704 is treated for development. Further thereon, a metal thin film 705 is formed in a thickness of 50 nm by vapor deposition (see FIG. 7B).

Figure 7C:
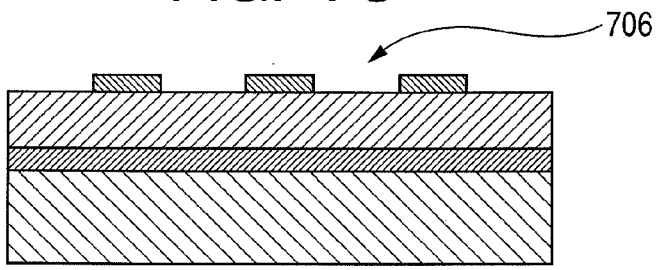

Finally, the element base plate is immersed in an EB resist solvent to obtain sensor element 706 by a lift-off method (see FIG. 7C).

In the above production process, metal fine structure 705 is patterned by an electron beam drawing apparatus, but the apparatus is not limited thereto. Metal fine structure 705 may be patterned by a FIB (focused ion beam) working apparatus or a like apparatus.

Figure 7D:
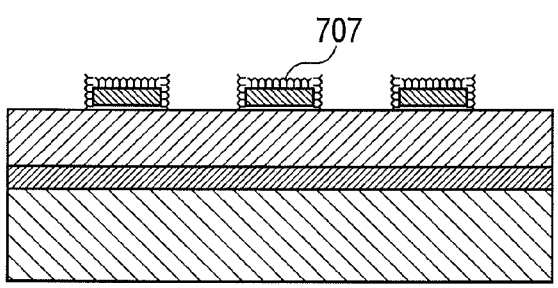

In the sensor element formed as described above, the surface of metal fine structure 705 is modified with an antibody. An example of the antibody is an anti-AFP antibody (anti-α-fetoprotein antibody). This anti-AFP antibody is immobilized on the surface of metal fine structure 705, and thereon an ethanol solution of 11-mercaptoundecanoic acid, which has a thiol group, is dropped by a spotter or the like to give a bared carboxyl group to the surface of metal fine structure 705. Subsequently, an aqueous solution of N-hydroxysulfosuccinimide and an aqueous solution of 1-ethyl-3-[3-dimethylamino]propyl carbodiimide hydrochloride are dropped by a spotter or the like onto the reaction region. Thereby, metal fine structure 705 comes to have an exposed succinimide group on the surface. Further, streptavidin is allowed to react to modify the surface of metal fine structure 705 with the streptavidin. Onto this metal fine structure 705, a biotin-containing anti-AFP antibody is immobilized. Thereby, metal fine structure 705 is modified by antibody 707 as illustrated in FIG. 7D.

With the sensor element 706 as prepared above, the antigen-antibody reaction is allowed to proceed and the optical spectrum is measured similarly as in Example 1, except that the light from the light source is polarized nearly in the short-pitch direction of the arrangement of the particles of metal fine structure 705 and the polarized light beam is projected to sensor element 706. Specifically, for the polarization, an optical element for converting the introduced light beam to a linear polarized light is placed on the light-introduction side of sensor element 706, whereby the electric field vector of the linear polarized light from the optical element is directed nearly parallel to the short-pitched arrangement lines of the particles of metal fine structure 705. The optical measurement is conducted with such an illumination system.

FIGS. 8A and 8B are schematic drawings illustrating schematically the element construction of the sensor element of this Example: FIG. 8A is a sectional view taken along line 8A to 8A in FIG. 8B, plan view. The sensor element illustrated in FIGS. 8A and 8B is produced through steps illustrated in FIGS. 7A to 7D. In FIGS. 8A and 8B, the same symbols as in FIGS. 7A to 7D are used to denote corresponding members.

As illustrated in FIGS. 8A and 8B, a particle of metal fine structure 705 in this Example is in a shape of a cube having a side of 50 nm. The particles of metal fine structure 705 are arranged at a pitch of 90 nm in a first direction and at a pitch of 600 nm in a second direction perpendicular to the first direction in an orthogonal lattice. The light beam emitted from the light source is polarized in the polarization direction E nearly parallel to the short-pitch arrangement lines of the particles of metal fine structure 705.

FIG. 9 spectra of light reflected by metal fine structure 705 formed on a simple quartz base plate. In FIG. 9, the ordinate indicates the reflectivity, and the abscissa indicates the wavelength. Curve 901 shows the reflection spectrum before adhesion of the target substance, and curve 902 shows the reflection spectrum after adhesion of the target substance. The change of the reflectivity spectrum by the target substance adhesion is calculated by subtracting the reflectivity spectrum after the adhesion from the reflectivity spectrum before the adhesion, and is shown as differential spectrum 903.

From the reflection spectra shown in FIG. 9, the resonance wavelength in metal fine structure 705 is estimated to be about 870 nm by assuming that metal fine structure 705 is surrounded by water. In this Example, in the sensor element, the arrangement pitch of the particles of metal fine structure 705 is 600 nm in the direction orthogonal to the light polarization direction. Therefore, the perpendicular incident light beam is diffracted by 90° at the wavelength of the mode of about 798 nm at the outside (water side) of the metal fine structure, and 876 nm at the base plate side.

The resonance wavelength in metal fine structure 705 observed in the reflection spectrum is considered to result from coupling of the mode of the localized plasmon resonance in the metal fine structure with the mode of transmission of the light introduced perpendicularly to the element surface, diffracted by 90°, and propagating nearly parallel to the element surface.

The product of the arrangement pitch of metal fine structure 705 and the refractive index of the dielectric layer or of the medium surrounding the metal fine structure 705 is equal to the wavelength of the plasmon resonance induced in metal fine structure 705. Here, the term "equal to" signifies not only "absolutely equal to" but also "nearly equal to". The term "nearly" herein signifies that the resonance wavelength of the sensor element resulting from coupling of the localized plasmon resonance mode and the resonator mode is within the range of resonance wavelength of simple metal fine structure 705.

Specifically, the resonance wavelength (about 870 nm) of the LSPR induced in metal fine structure 705 is nearly equal to the wavelength 876 nm for causing the 90°-diffraction of the incident light at the substrate side. The product of the arrangement pitch 600 nm of metal fine structure 705 and the refractive index 1.46 of the dielectric layer, namely 876 nm, is nearly equal to the resonance wavelength 870 nm of LSPR induced in the metal fine structure before adhesion of the target substance.

In this Example, in the sensor element, the resonance is induced at about 800 nm to 900 nm near the above-mentioned resonance wavelength caused in metal fine structure 705.

With resonator layer 703 of about 300 nm thick, the effective length of the resonator is 510 nm in consideration of phase change at the reflection at the resonator end faces. In this resonator layer 703, the wavelength of the resonance induced in resonator 703 is about 1020 nm (reflection spectrum 904). With this constitution, the resonance mode of the resonator (resonance wavelength: 1020 nm), the LSPR resonance (resonance wavelength: about 870 nm), and the mode of 90°-diffraction are coupled together, resulting in the resonance wavelength of about 830 nm of the sensor element of this Example.

The sensor element of this Example gives reflection spectrum 905 before adhesion of the target substance, and gives the reflection spectrum 906 after adhesion thereof. The change of the reflection spectrum by adhesion of the target substance is shown by differential spectrum 907. Form this result, the sensor element of this Example gives maximum differential of 0.8, improved in the sensing sensitivity in comparison with the performance of single metal fine structure (maximum differential: about 0.4)

In this Example, the resonance wavelength is 830 nm, but is not limited thereto. The construction of metal fine structure 705 is not limited to that illustrated in the drawing. Further, the reflectivity near the resonance wavelength of metal fine structure 705 is preferably set to deepen and sharpen the peak in constructing the resonator of the sensor element.

The shape of the respective metal fine particles constituting the metal fine structure 705 is not limited to be cubical, but may be polygon-columnar, or round-columnar. With higher symmetry of the fine particles, the dependency of the element on light polarization is decreased. The arrangement of the metal fine structure 705 is not limited to be in the orthogonal lattice arrangement, but may be in a triangular or hexagonal lattice arrangement for decreasing the dependency of the element on light polarization.

In the sensor element of this Example, the mode of the metal fine structure and the mode of the resonator combined thereto are coupled and further therewith the light diffracted at a diffraction angle near 90° is coupled. Thereby the peak width of the optical spectrum is decreased, while the amount of shift of the optical spectrum caused by the reaction is retained. As the result, the sensing sensitivity is increased, and further the production of the sensor element can be made easier owing to the simple element construction.

Next, a sensing apparatus employing a sensor element of the present invention is described below.

Figure 10:
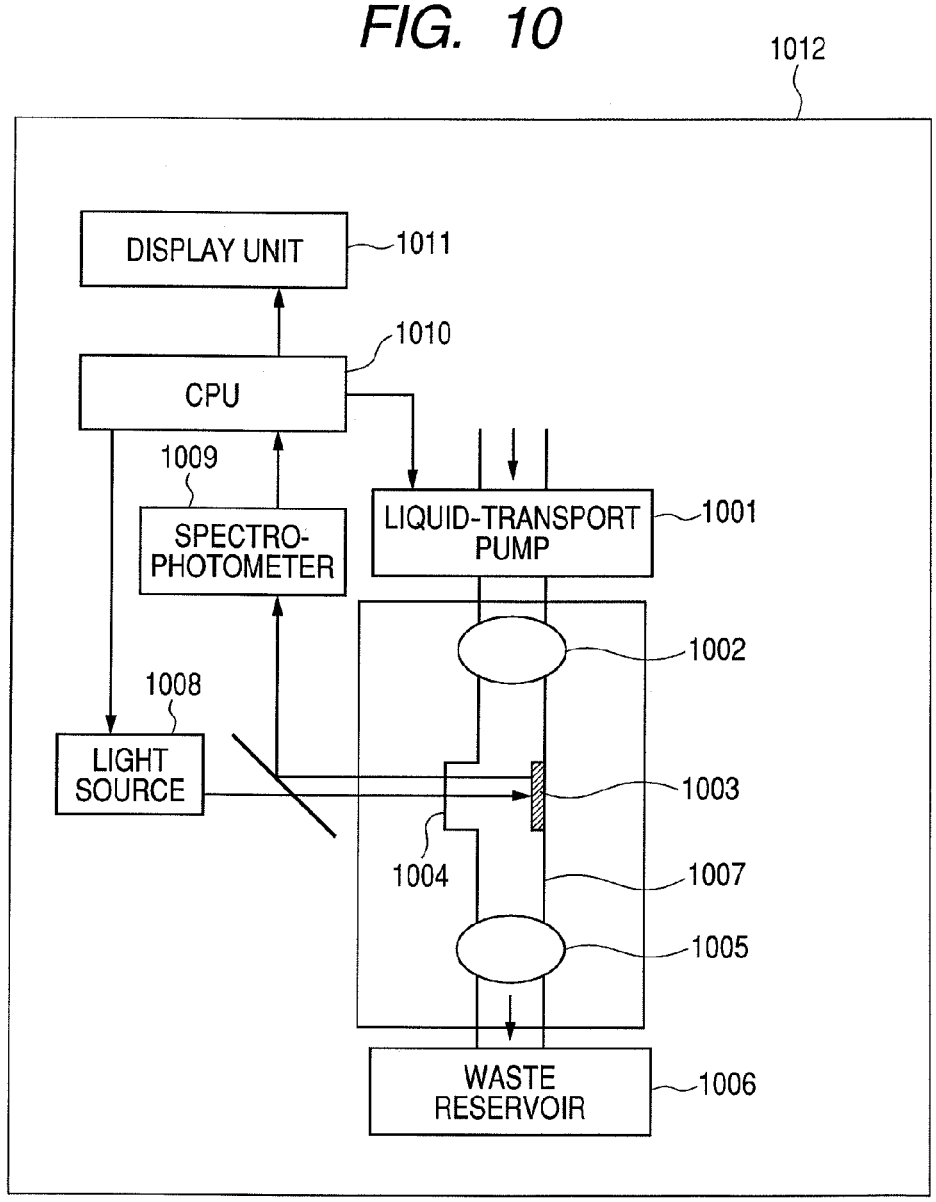
FIG. 10 is a block diagram of an example of a sensing apparatus employing a sensor element of the present invention.

FIG. 10 illustrates a sensing apparatus employing a sensor element of the present invention. In FIG. 10, Sensing apparatus 1012 comprises an optical system containing flow channel 1007, light source 1008, and spectrophotometer 1009; and measurement processing system containing CPU (central processing unit) 1010, and display unit 1011.

Flow channel 1007 has liquid transport pump 1001, liquid inlet 1002, reaction well 1004, liquid outlet 1005, and waste reservoir 1006.

A reference liquid and a specimen liquid are fed by liquid transfer pump 1001 through liquid inlet 1002 and are introduced into reaction well 1004 in which sensor element 1003 is placed. The reference liquid and the specimen liquid are allowed to flow in contact with sensor element 1003 in reaction well 1004, and are discharged from reaction well through outlet 1005 to waste reservoir 1006.

The light beam emitted from light source 1008 is projected to sensor element 1003 in reaction well 1004. Light source 1008 may be a tungsten lamp, but is not limited thereto. A polarizer may be inserted to the optical illumination system to polarize the projected light beam. Light source 1008 is not limited thereto, insofar as the light source emits the light in the measurement wavelength range.

The light beam emitted from light source 1008 is reflected by sensor element 1003, and introduced by reflection by a mirror to spectrophotometer 1009. Spectrophotometer 1009, which is an optical detection element, measures spectroscopically the light reflected by sensor element 1003.

The data obtained by spectrophotometer 1009 is supplied to CPU 1010. CPU 1010 processes the data. The result of the processing is displayed as the measurement result on display unit 1011. CPU 1010 sends control signals to light source 1008 and liquid transport pump 1001.

The above sensor element 1003 is a sensor element of the present invention. Sensing apparatus 1012 employing sensor element 1003 is capable of sensing (e.g., refractive index sensing, and bio-sensing) with a high sensitivity.

The sensing can be conducted through the steps below.

(Step 1) Detection of light beam projected to and reflected by the chemical sensor element in the absence of the target substance adhering to the chemical sensor element.

(Step 2) Detection of light beam projected to and reflected by the chemical sensor element in the presence of the target substance adhering to the chemical sensor element.

(Step 3) Calculation of differential between the optical spectrum of the reflected light detected in the First Step and the optical spectrum of the optical spectrum detected in the Second Step.

In the case where the sensor element described in Example 2 is employed, the light beam from light source 1008 is polarized in the polarization direction nearly parallel to the short-pitch direction of the arrangement of the metal fine structure particles, and the polarized light beam is projected to the sensor element for the optical spectrum element.

As described above, in the chemical sensor element of the present invention, the mode of the surface plasmon resonance which gives a large shift of the spectrum caused by the reaction and the mode of the resonator which gives a spectrum of a small line width are coupled together to obtain a smaller spectrum line width with a large shift of the spectrum caused by the reaction. Thereby, the obtained spectrum has characteristics of the both modes to give spectrum of a small line width. Therefore, the chemical sensor element having a resonator construction is capable of measurement with higher sensitivity than prior art techniques by decreasing the line width of the resonance spectrum and enlarging the extent of shift of the resonance spectrum.

In the system in which the resonance wavelength $\lambda 1$ of the resonator is equal to the resonance wavelength $\lambda 0$ of the surface plasmon induced in the metal fine structure, particles causing the plasmon resonance are placed at the position where the "node" of the standing wave is inherently formed. However, the particles themselves in the resonance state functions as a wave source and serves as the "loop" of the plasmon resonance mode, and cannot be consistent with the resonator mode. Therefore, in the system in which the resonance wavelength $\lambda 1$ of the resonator is equal to the wavelength of surface plasmon wavelength $\lambda 0$, the plasmon resonance cannot be excited, and the resonance peak almost disappears from the reflection spectrum to interrupt the sensing. On the other hand, in the chemical sensor of the present invention, in which the resonance wavelength $\lambda 1$ of the resonator is different from the wavelength $\lambda 0$ of the surface plasmon resonance, the both modes can be consistent.

The line width of the plasmon resonance is usually in the wavelength range of ±25% of the resonance wavelength. Therefore, to excite a plasmon resonance, the projected light has a wavelength preferably within the range of the spectrum line width of the plasmon resonance. Therefore, in the system in which the projected light has a wavelength within the wavelength range within the plasmon resonance line width to excite the resonator mode and the plasmon mode simultaneously, the resonance wavelength of the resonator is preferably within the wavelength range of the line width of the plasmon resonance. In the present invention, the resonance wavelength of the resonator is set within ±25% of the wavelength of the surface plasmon resonance $\lambda 0$, whereby the resonator mode and the plasmon resonance mode can be excited surely simultaneously. Incidentally, the line width of the plasmon resonance herein signifies the wavelength range of half of the half-width in the plus and minus directions from the central wave length.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-286102, filed Nov. 2, 2007, which is hereby incorporated by reference herein in its entirety.

The invention claimed is:

1. A chemical sensor element containing a resonator having a first reflector, in which particles of a fine metal structure are arranged two-dimensionally and periodically, counterposed with interposition of a dielectric layer to a second reflector, wherein dimensions of the sensor provide for a resonance wavelength of a resonator, as determined where the entire first reflector is replaced by a metal thin film having the same thickness as the metal fine structure, that is different from a surface plasmon resonance wavelength induced in the metal fine structure and is within ±25% of the plasmon resonance wavelength; and a mode of a surface plasmon resonance excited in the metal fine structure is coupled with a mode of the resonator, as determined where the entire first reflector is replaced by a metal thin film having the same thickness as the metal fine structure, and wherein the resonance wavelength $\lambda 1$ of the resonator is represented by an equation:

$$m\lambda_1 = 2nL + (\phi_1/2\pi)\lambda_1 + (\phi_2/2\pi)\lambda_1,$$

where n is a refractive index of the dielectric layer and L is a thickness of the dielectric layer, $\lambda_1$ is the resonance wavelength of the resonator in which the entire of the first reflector is replaced by the metal thin film, $\phi_1$ is a change of phase caused by reflection of light propagating in the dielectric layer by the metal thin film, $\phi_2$ is a change of phase caused by reflection of the light propagating in the dielectric layer by the second reflector, and m is a natural number.

2. The chemical sensor element according to claim 1, wherein the second reflector is comprised of a metal.

3. The chemical sensor element according to claim 1, wherein the metal fine structure or the second reflector is comprised of any one selected from the group consisting of gold, silver, copper, platinum and aluminum.

4. The chemical sensor element according to claim 1, wherein a particle of the metal fine structure is in a shape of a rectangular solid, a polygonal column, or a round column.

5. The chemical sensor element according to claim 1, wherein the particles of the metal fine structure are arranged in triangular lattice.

6. The chemical sensor element according to claim 1, wherein a product of an arrangement pitch of the metal fine structure and a refractive index of the dielectric layer or a refractive index of a medium surrounding the metal fine structure is equal to the wavelength of the plasmon resonance induced in the metal fine structure.

7. A sensing apparatus, comprising:

a chemical sensor element according to claim 1, a light source for projecting a light beam perpendicularly to a face of the resonator constituting the chemical sensor element on which the metal fine structure is formed, and a light detecting element for detecting reflected light from the chemical sensor element.

8. The sensing apparatus according to claim 7, wherein the apparatus further comprises an optical element for converting the light projected to the chemical sensor element into linear polarized light, and the light polarization is orthogonal to a pitch direction of an arrangement of the metal fine structure.

* * * * *